US012685518B2

(12) United States Patent
Baumann et al.

(10) Patent No.: US 12,685,518 B2
(45) Date of Patent: Jul. 21, 2026

(54) METHOD FOR THE NON-INVASIVE CAPTURE OF THE TEMPORAL DEVELOPMENT OF A STATE OF A TISSUE STRUCTURE

(71) Applicant: Compremium AG, Muri b. Bern (CH)

(72) Inventors: Vincent Boris Baumann, Gümligen (CH); Peter Nuot Frei, Duliken (CH); Ulrich Baumann, Münsingen (CH)

(73) Assignee: COMPREMIUM AG, Bern (CH)

( * ) Notice: Subject to any disclaimer, the term of this patent is extended or adjusted under 35 U.S.C. 154(b) by 0 days.

(21) Appl. No.: 18/683,201

(22) PCT Filed: Aug. 11, 2022

(86) PCT No.: PCT/EP2022/072593
§ 371 (c)(1),
(2) Date: Feb. 12, 2024

(87) PCT Pub. No.: WO2023/020941
PCT Pub. Date: Feb. 23, 2023

(65) Prior Publication Data
US 2024/0341733 A1 Oct. 17, 2024

(30) Foreign Application Priority Data
Aug. 17, 2021 (CH) ................................ 70175/2021

(51) Int. Cl.
*A61B 8/00* (2006.01)
*A61B 8/08* (2006.01)
(Continued)

(52) U.S. Cl.
CPC .............. *A61B 8/565* (2013.01); *A61B 8/429* (2013.01); *A61B 8/463* (2013.01); *A61B 8/468* (2013.01);
(Continued)

(58) Field of Classification Search
CPC ......... A61B 8/565; A61B 8/429; A61B 8/463; A61B 8/468; A61B 8/485; A61B 8/5207;
(Continued)

(56) References Cited

U.S. PATENT DOCUMENTS 10,925,583 B1 * 2/2021 Moehring ................ A61B 8/08
2004/0116812 A1 6/2004 Selzer et al.
(Continued)

FOREIGN PATENT DOCUMENTS

JP 2006055326 A 3/2006
JP 2008272025 A 11/2008
(Continued)

OTHER PUBLICATIONS

SocketCam Camera-Based Barcode Scanners, 2025 Socket Mobile, Inc; https://www.socketmobile.com/readers-accessories/product-families/socketcam (Year: 2025).*
(Continued)

*Primary Examiner* — Alexei Bykhovski
(74) *Attorney, Agent, or Firm* — Lerner David LLP

(57) ABSTRACT

In a method for the non-invasive capture of a temporal development of a state of a tissue structure, first measurement data of the body region (1) are recorded non-invasively and first image data are generated from the recorded measurement data. This first image data is pre-processed locally with the aid of a first local terminal device (100.1) and transmitted together with first identification data from the first local terminal device (100.1) to a server (10) for storage. At a later time, image data stored using second identification data is retrieved from the server (10) and displayed on the second local terminal device (100.2). This is followed by a non-invasive recording of second measurement data of the body region (1) to generate second image data.

25 Claims, 10 Drawing Sheets

(51) Int. Cl.
  *A61B 90/00*        (2016.01)
  *A61B 90/96*        (2016.01)

(52) U.S. Cl.
  CPC ............ *A61B 8/485* (2013.01); *A61B 8/5207*
    (2013.01); *A61B 8/5223* (2013.01); *A61B*
    *90/96* (2016.02); *A61B 2090/3937* (2016.02)

(58) Field of Classification Search
  CPC .................. A61B 8/5223; A61B 90/96; A61B
    2090/3937; A61B 5/6843; A61B 8/5269;
    A61B 5/0077; A61B 8/4427; A61B
    8/465; A61B 8/08; A61B 8/4272; A61B
    5/03; A61B 8/5215; G16H 30/20; G16H
    30/40; G16H 40/67; G16H 50/30; G06T
    2207/10016; G06T 2207/20081; G06T
    2207/20084; G06T 2207/30088; G06T
    7/0016; G06T 7/73; G06T 2207/30004;
    G06T 2207/10132; G06V 40/00
  See application file for complete search history.

(56)                References Cited

U.S. PATENT DOCUMENTS

| | | | |
|---|---|---|---|
| 2008/0269605 | A1 | 10/2008 | Nakaya |
| 2011/0200227 | A1* | 8/2011 | Bogoni .................. G16H 30/20 |
| | | | 382/103 |
| 2013/0116565 | A1* | 5/2013 | Miyama ............... A61B 8/5276 |
| | | | 600/443 |
| 2013/0177226 | A1 | 7/2013 | Park et al. |
| 2015/0178921 | A1 | 6/2015 | Hashimoto et al. |
| 2017/0109473 | A1* | 4/2017 | Kulon .................... G16Z 99/00 |
| 2017/0256082 | A1 | 9/2017 | Nabatame et al. |
| 2018/0204028 | A1* | 7/2018 | Choi ........................ A61B 8/54 |
| 2019/0038135 | A1 | 2/2019 | Lee et al. |
| 2020/0315583 | A1 | 10/2020 | Baumann |
| 2020/0327671 | A1* | 10/2020 | Arbel ....................... G06N 3/08 |
| 2021/0007709 | A1 | 1/2021 | Endo et al. |
| 2024/0138810 | A1* | 5/2024 | Huang .................. A61B 8/429 |

FOREIGN PATENT DOCUMENTS

| | | |
|---|---|---|
| JP | 2012034811 A | 2/2012 |
| JP | 2016087020 A | 5/2016 |
| JP | 2017153818 A | 9/2017 |
| JP | 2021504086 A | 2/2021 |
| WO | 2019106535 A1 | 6/2019 |

OTHER PUBLICATIONS

Non-invasive measurement of muscle comparment; Sellei R.M. et al.
Commpression sonography for non-invasive measurement; Bloch Andreas et al.

* cited by examiner

120

151

190

185

METHOD FOR THE NON-INVASIVE CAPTURE OF THE TEMPORAL DEVELOPMENT OF A STATE OF A TISSUE STRUCTURE

FIELD OF THE INVENTION

The invention relates to a method for the non-invasive capture of a temporal development of a state of a tissue structure. The invention further relates to a system and a computer program for carrying out the method.

DESCRIPTION OF RELATED ART

In the context of medical diagnostics, it is often useful to track the development of the state of a tissue structure over time in order to obtain basic information for a diagnosis and to ensure that therapeutic measures are taken in good time, while at the same time avoiding unnecessary measures.

For example, if there is a possibility of acute compartment syndrome (often referred to as loge syndrome), the compartment or compartments in question should be monitored after a traumatic impact. For this purpose, a series of examinations are carried out at intervals of several hours. The results of the respective examination and the development over time are used as the basis for a diagnosis and as the basis for the decision on surgical treatment. Various techniques are known for the examination. The simplest is manual palpation to capture the elastic properties of the compartment. Here, the examining physician relies primarily on his or her experience, which means that different specialists will come to different conclusions. Greater reliability can be achieved with pressure measurements directly in the compartment-however, these examinations are invasive and therefore painful and are generally associated with a risk of infection.

In WO 2019/106535 A1 (U. Baumann, V. Baumann), the combination of a pressure measuring device and an ultrasound measuring unit was therefore proposed in order to systematically and non-invasively capture elastic properties of compartments, among other things. Such a combination is also suitable for obtaining basic information for the diagnosis of compartment syndrome.

If examinations of a tissue structure are carried out at different times and by different specialists, there is a risk that the modalities of different examinations, e.g. the location of the examination or corresponding parameters, may differ, resulting in different results. This makes it particularly difficult to compare several examination results on the same tissue structure, e.g. to obtain trend information. Especially with non-invasive examinations, e.g. those carried out using hand-held devices, systematic differences in positioning can arise.

SUMMARY OF THE INVENTION

The task of the invention is therefore to create a method belonging to the technical field mentioned at the beginning for the non-invasive capture of a temporal development of a state of a tissue structure, which provides improved basic information for diagnostic purposes based on several, temporally offset examinations.

The solution to the problem is defined by the features of claim 1. According to the invention, a method for the non-invasive capture of a temporal development of a state of a tissue structure comprises the following steps:

a. non-invasive recording of first measurement data of a body region to be examined and generation of first image data from the recorded measurement data;

b. local pre-processing of the first image data using a first local terminal device;

c. transmitting the pre-processed first image data and the first identification data from the first local terminal device to a server for storage;

d. at a later point in time retrieving stored image data from the server with a second local terminal device using second identification data;

e. display the retrieved image data on the second local terminal device;

f. non-invasive recording of second measurement data of the body region to generate second image data.

The procedure is particularly suitable for humans, but can also be used in veterinary medicine.

Non-invasive Capture or non-invasive recording of measurement data includes steps that are carried out without an incision and without inserting devices or catheters into the body, i.e. purely externally. In particular, this includes measurements that are taken on the outside of the body or using suitable fields or radiation (e.g. sonography, X-ray examinations, MRI, OCT, etc.).

The identification information is, for example, a number or an alphanumeric character string, but it can also be image data, for example. Preferably, the identification data does not allow any conclusions to be drawn about the identity (e.g. the name, an insurance number or similar) of the patient. Particularly sensitive patient information can be protected in this way, and the assignment can only be made locally, but not on the basis of data transmitted or stored by the server.

The first and second image data are in particular sectional images, e.g. in a plane that forms an angle of 60°-120° to a tangential plane to the body surface at the measurement location. However, 3-dimensional images can also be generated as first and second image data. The first and second image data can each comprise one or more images.

During local pre-processing of the first and second image data, in particular filters are applied to the image data, e.g. to increase contrast, reduce image noise or enhance contours. For example, well-known HAF filters (Histogram Adaptive Fuzzy Filters) can be used. The image section can also be selected automatically. Additional information can be obtained from the image data during pre-processing, e.g. intensity curves and/or histograms. The image data can also be compressed, for example. Depending on the basis on which the first image data was obtained and the form in which it is available, more or fewer steps are required during pre-processing.

The transmission of the pre-processed first image data and the first identification data from the first local terminal device to the server can take place directly via a data network to which both the first local terminal device and the server are connected, or gateway is used which is local in relation to the first local terminal device, with which the first local terminal device communicates and which takes over the data transmission to and from the server for all local terminal devices. In particular, the data is transmitted via a secure Internet connection (e.g. using Transport Layer Security-TLS). For example, the local terminal device is connected wirelessly to a router via a (again protected) WLAN connection. However, transmission via a mobile network is also possible, for example. If a gateway is used, the data to be transmitted can be temporarily stored locally. However, because the image data is not necessarily retrieved later using the same terminal device and because a different gateway can also be used (e.g. if the patient is transferred to another department or hospital), the data should be transmitted to the server within a maximum period of time so that it can be retrieved at a later point in time.

Local intermediate storage can also take place on the first local terminal device itself, especially if no transmission to the gateway or server is temporarily possible. In certain cases, e.g. if the connection is interrupted for a longer period of time, the data required for the second, later measurement (e.g. the first image data) can then be used from the local cache-provided that the same local terminal device is used again.

The pre-processed first image data or further processed image data obtained from it is linked to the first identification data after storage.

The first local terminal device and the second local terminal device may be two devices or the same device, e.g. depending on whether the patient is examined at the same location and/or by the same person during the examinations at different times. Data storage on the server ensures that the second measurement data can be obtained precisely and reliably in the same way in both cases. The same applies to any other local terminal devices that are used to examine the patient over time.

If the first and second identification data are unique numeric or alphanumeric data, the stored image data can be retrieved directly using this data. If the information is of a different type, e.g. image data, the first identification data and the second identification data will generally not be identical. In this case, a comparison operation is performed on the server in order to assign the first identification data to the second identification data. The stored image data can be the pre-processed first image data previously transmitted by the first local terminal device or image data that has been further processed on the server. In addition to the image data, further information linked to the first identification data can be retrieved.

The display of the retrieved image data on the second local terminal device facilitates the acquisition of the second measurement data in that the user—regardless of whether he has performed the first examination himself or not—can use this image data to easily ensure that he performs the second examination at the same examination site and with the same examination parameters, e.g. with regard to the orientation of a sectional plane. This image data can thus serve as a navigation aid during the second examination to ensure that the same tissue structure is examined and the same image section is generated. In addition to the image data, further information can be stored on the server and retrieved by the second terminal device to ensure the repeatability of the measurement, e.g. distance information on the body surface, photos of the measurement site and/or a video sequence documenting the measurement process during the first examination.

The same local terminal device and the devices integrated in it or connected to it, namely the device for recording the measurement data, can thus be used to carry out successive examinations on the same patient or on different patients, whereby correct assignment of the image data and measurement data is always guaranteed.

The method is particularly advantageous for series of examinations that involve carrying out several examinations of the same kind of the same body region at intervals of several minutes to several hours. The method is also particularly advantageous for examinations that are carried out using hand-held devices, because in these cases it can be particularly difficult to ensure the same framework conditions for several staggered examinations without support by imaging.

The method according to the invention is not limited to carrying out two measurements; three or more measurements can be carried out in the same way, at a respective time interval, on the same, two or more local terminal devices.

Preferably, when the second measurement data is recorded, the second image data is displayed in real time on the second local terminal device, in particular simultaneously with the retrieved image data.

This enables particularly accurate monitoring of the recording of the second measurement data, in particular increased visual precision during the measurement process. This increases the inter- and intra-observer reliability of the procedure. For example, the operator can immediately recognize whether the same tissue structure is being examined with essentially the same image section. Deviations in examination parameters can also generally be easily recognized based on the generated and displayed images. Due to the real-time display, adjustments made by the operator have an immediate effect, resulting in intuitive and smooth operation.

In a preferred embodiment of the method according to the invention, the non-invasive recording of the first measurement data comprises a sonographic measurement process.

Such measurements can be carried out on practically all patients, including unborn babies, without any expected harmful consequences. They are suitable for examining various tissue structures, including sensitive ones, and can be carried out using relatively inexpensive technology and compact devices. In addition, continuous repetitive imaging can be performed easily, allowing individualized, risk-based and reliable monitoring of the examination process.

Instead of or in addition to sonographic measurements, other measurement procedures can be performed that can provide measurement data suitable for obtaining image data of the tissue structure to be examined, including, for example, X-ray examinations (CT), magnetic resonance imaging (MRI), optical coherence tomography (OCT), etc.

Advantageously, the pre-processed first image data is displayed on the local terminal device, and further first measurement data can be recorded based on the display.

If the other first measurement data are based on a different measurement principle, the display of the image data enables precise positioning of the corresponding measuring device in particular. It is particularly preferable for the image data to be displayed in quasi-real time, as is readily possible based on sonography, for example.

The first image data can be pre-processed for display on the local terminal device and for transmission to the server in the same or different ways. It is also possible to generate differently pre-processed image data and transmit both to the server for storage. For example, first pre-processed image data can be retrieved later and displayed on the second local terminal device, while second pre-processed image data is stored on the server for reference or diagnostic purposes and is not required for recording second measurement data.

The non-invasive recording of the first measurement data can in particular comprise a measurement of a contact pressure.

The values of the contact force are the mentioned other first measurement data. The contact force, which is exerted essentially perpendicular to the body surface, for example, can be used to determine the elastic properties of the tissue structure under investigation.

Other measurement data can also be obtained and linked to the first measurement data used to obtain the image data. This includes, for example, information on heart rate, blood pressure, blood oxygen saturation, body temperature, etc., possibly in relation to the location of the respective examination.

To obtain information on an elastic state of the tissue structure, dimensions can be determined both in the first image data and in the second image data, each with at least two different contact pressure forces.

Depending on the purpose of the application and the available image data, the dimensions can be point positions, lengths, areas or volumes. Ratio sizes are also possible, e.g. corresponding to the eccentricity of an elliptical surface or a length ratio of two parallel lines or lines at a certain angle.

By comparing the dimensions resulting from different contact forces, a direct measure of the elasticity (or stiffness) of the tissue structure under investigation can be obtained. For example, a strong compression of a tissue structure due to the application of force usually means that it has a high elasticity overall, while a low compression indicates a low elasticity (or high stiffness). If the tissue structure comprises compartments, a low elasticity can indicate a high internal pressure in these compartments in particular. In this context, a compartment is understood to be a closed cavity or receiving space inside the body in which a certain pressure prevails, which may differ fundamentally from the pressure in the surrounding tissue. Of interest here are compartments that can be elastically deformed by the application of an external force. Such compartments include in particular the compartments of muscle tissue, blood vessels and organs (e.g. the liver or the brain).

To determine the dimensions, a manual marking process can be carried out on the displayed first image data and second image data.

During the manual marking process, an operator defines one or more points, lines, areas and/or volumes in the displayed image data, in particular via a user interface of the first local terminal device and/or the second local terminal device. This results in length, area or volume values or other geometric values, such as angles or eccentricities, either directly or by means of arithmetic operations.

To support the manual marking process, a representation of an intensity curve of the first or second image data along a line is displayed.

It has been shown that such a representation is particularly helpful when defining positions or distances that are determined by two positions, as it improves the reproducibility of the marking process. The intensity curve itself can be displayed, but it will often be advantageous if this is smoothed by suitable algorithms, e.g. by a binning process.

Advantageously, a proposal for markings to be made during the marking process is automatically generated on the basis of the first or second image data.

The proposal serves as a starting point for manual marking by the operator and thus facilitates the marking process. Nevertheless, the responsibility for marking remains entirely with the operator.

The proposal is generated in particular with the help of common image processing methods, e.g. for recognizing edges. However, it can also be based on a (supervised) machine learning process, e.g. with the help of an artificial neural network, whereby previous markings made by the same or other operators and the corresponding image data serve as training data for training and improving the model.

The dimensions can also be determined automatically on the basis of the first image data or second image data.

The determination of the dimensions can—like the generation of the proposal—be based in particular on common image processing methods and/or a machine learning process. It is also possible to initially provide a manual marking process in an overall system for carrying out the method according to the invention and only allow automatic determination for a specific measuring process when the adjustments made by the operators to automatically generated proposals statistically fall below a predetermined level.

The location of the measurement to be performed can be determined by the operator, e.g. by a corresponding marking process on the image data, but it can also be determined automatically. In a preferred embodiment, the location is specified by the operator during the first measurement and is then determined automatically during subsequent measurements using the image information, e.g. by matching the most recent image data with the first image data using a matching process and transferring the location of the measurement from the first image data to the most recent image data. Particularly in the case of subsequent measurements, the measurement and any subsequent steps can thus be carried out fully automatically as soon as the corresponding measurement data can be recorded, e.g. as soon as a measuring head of a measuring unit is suitably positioned. This positioning can be supported by the system, e.g. by displaying the measurement location for the measuring head with the aid of a projected marking on the body surface or with the aid of augmented reality techniques.

In preferred embodiments, a first value for the elastic state of the tissue structure is determined from the determined dimensions at the different contact forces based on the first measurement data and a second value for the elastic state of the tissue structure is determined from the determined dimensions at the different contact forces based on the second measurement data, the first value and the second value representing a measure for a deformability of the tissue structure.

The values for the elastic state of the tissue structure can be values that are a measure of the elasticity of the examined tissue or values that are a measure of the stiffness of the examined tissue.

It is particularly preferable to use an ultrasonic measuring head with an integrated pressure measuring device, such as that known from EP 3 716 842 A1 (Veinpress GmbH), to simultaneously generate and display an image of the tissue structure to be examined and measure the contact pressure exerted, corresponding to a specific contact pressure. As soon as the required pressure is generated, the dimensions can be determined on the basis of the image. In the case of manual marking, this can be supported by immediately generating a still image of the current ultrasound image when a predefined pressure value is reached and displaying it for the subsequent marking process. If the dimensions are determined automatically, the image at the corresponding pressure value can be used directly as a basis.

The generation of a still image or automatic evaluation can be repeated for several predefined pressure values. In this case, the operator only has to place the measuring head at the point corresponding to the tissue structure to be examined, slowly increase the contact pressure manually, e.g. for a few seconds, and then lower it again. The still images generated at the specified pressure values are then displayed and the dimensions can be determined.

One possible definition for a value for the elastic state of the tissue structure is the so-called "CP score", defined as follows:

7

$$CP = 100 - 100 \cdot \frac{D_1 - D_2}{D_1} [\%] = 100 \frac{D_1}{D_2} [\%],$$

where $D_1$ denotes an expansion of the compartment at a first, lower pressure $p_1$ and $D_2$ denotes an expansion of the compartment along the same line in the direction of the application of force at a second, higher pressure $p_2$. Values of $p_1$=10 mmHg and $p_2$=80 mmHg have proven to be suitable for the examination of compartments that may be affected by compartment syndrome.

A CP score of 0% corresponds to (theoretically) complete compression along the line mentioned, i.e. high elasticity (or low stiffness). A CP score of 100% corresponds to no compression along the line mentioned, i.e. low (or no) elasticity (or maximum stiffness).

In principle, the comparison of a compressed state with an uncompressed state (i.e. with no contact pressure) would be of interest. However, because a certain minimum pressure of the ultrasound probe on the body surface is necessary to obtain a usable ultrasound image, a low lower pressure is suggested here.

The CP scores at different points in time provide valuable basic information for the diagnosis of compartment syndrome. Their absolute value can be compared with threshold values and/or the temporal course, in particular the temporal gradient of the CP score, can be considered in order to draw conclusions. Due to the definition as a ratio, systematic errors can be eliminated from the outset.

Modified CP scores are possible for characterizing other tissue structures, in which the dimensions are determined at other specified pressure values, for example. The measure can also be generalized to take into account measurements at more than two pressure values.

The method according to the invention can be used in particular to obtain information on the elastic state of compartments. Such information is very valuable with regard to the detection of compartment-related signs of disease. In particular, the method can provide basic information for the diagnosis of compartment syndrome (or loge syndrome). In addition to information on the elastic state, which includes in particular the aforementioned values on the elastic state of the tissue structure, other measurement data, e.g. on the blood-oxygen content in the area of the examined tissue structure, can also be collected and processed.

The body region to be examined is therefore, for example, a body region in which compartment syndrome can occur. This includes the forearm and lower leg region and the abdomen. However, the procedure can also be used in other regions of the body at risk and in connection with other clinical pictures.

Preferably, time information is transmitted to the server for storage with the pre-processed first image data and the first identification data.

The time information is linked to the image data and the identification data on the server. In addition to the information mentioned, further data can be transmitted to the server for storage, e.g. measurement parameters or identification data relating to the person carrying out the measurement.

Preferably, a medically relevant point in time, in particular a point in time of a traumatic impact, is captured and transmitted to the server for storage.

If information about the typical course of symptoms triggered by a traumatic impact, e.g. acute compartment syndrome, is known, it can be of great benefit if the time of the traumatic impact is known and included in the diagnostic assessment. The point in time of the traumatic impact is therefore important additional basic information for a subsequent diagnosis.

If measurement data is already available, it can be compared with the typical courses, taking into account the captured time of the traumatic impact. This comparison can be used, for example, to generate a corresponding improved measure for characterizing the state of the tissue structure.

In the case of an impending but not yet diagnosed acute compartment syndrome, consideration of the traumatic impact can enable more reliable or earlier recognition of a development leading to the acute compartment syndrome or a harmless course. In the case of chronic compartment syndrome, the first time that pain occurs during sporting activity or as part of standard examination protocols can be equated with the traumatic impact for the purpose of analysis.

Taking the captured medically relevant point in time into account, a recommendation can also be generated for a time of capturing the second measurement data.

For example, there are periods of time in typical courses of disease in which a close-meshed examination is indicated, while in other periods frequent examinations provide little insight. The recommendations generated can thus be used to ensure that the necessary information is captured at an early stage, while at the same time avoiding unnecessary effort and unnecessary stress for the patient.

Preferably, the body region to be examined is provided with an individual marking before the first measurement data are recorded. This marking is read by means of a first reading device, and the first identification data is generated on the basis of the read marking. Before the stored image data are retrieved, the marking is read again using a second reading device and the second identification data are generated using the read marking.

The marking ensures the correct assignment of several measurement data recorded at different times to the same patient or to the same body region. It can generally designate the body region to be examined, e.g. a limb. In this case, the subsequent examination is based on further information, e.g. physiological information. However, the marking can also be placed directly at the site of the examination to be performed so that the site to be examined is immediately identified.

The marking can be universally unique, e.g. by including a centrally assigned, unique identification number. However, statistical uniqueness is sufficient so that individual patients or body parts to be examined at a treatment location (e.g. a hospital) can be distinguished with a probability bordering on certainty, if necessary with recourse to further information.

The identification information, e.g. a number or an alphanumeric character string, corresponds in particular to the content or part of the content of the marking. Depending on the marking, however, it may also be image data, for example.

The first reading device and the second reading device may be two devices or the same device, e.g. depending on whether the patient is examined at the same location and/or by the same person during the spaced examinations.

Accordingly, a particular patient can be examined several times with the same equipment or with different equipment based on the individual marking, without the operators having to make a manual assignment.

Preferably, a tag with a unique identification is attached, in particular stuck, to the body region to be examined in order to provide it with the individual marking.

In particular, the tag can comprise optically readable information (e.g. a barcode or dot-matrix code) and/or electrically readable information (e.g. using RFID technology).

As an alternative to such a tag, it is also possible to mark the body region using a stamp or a "random" felt-tip pen pattern, for example. It is also possible to carry out multiple identification using optical images of the patient's face (facial recognition) or, as the case may be, the body region itself, although this raises questions regarding the anonymization of the data. It is also possible to use other biometric features (e.g. fingerprints) of the patient.

Preferably, the first reading device and the second reading device are optical reading devices, in particular cameras.

The reading device can be integrated into a measuring head for recording the first or second measurement data, e.g. an ultrasonic head. However, it can also be integrated into the first or local terminal device, or it can be a stand-alone device. Instead of cameras, dedicated reading devices can be used to capture standardized codes, e.g. barcodes or dot-matrix codes.

In further embodiments, the first reading device and the second reading devices comprise transponders for interacting with RFID transponders in a corresponding tag. In this case, the reading devices are particularly easy to integrate into the measuring heads.

In principle, the reading device can also be a keyboard or a touchscreen. If the individual marking comprises optically directly detectable information such as numbers or character strings, in particular in addition to machine-readable information, this can be read and typed in by an operator. The presence of machine-readable information is nevertheless advantageous because it minimizes the risk of errors.

Instead of being based on an individual marking on the body region to be examined, the identification data can also be obtained from other information or documents, e.g. by reading or typing information on a wristband, on a label attached to another body region or on a patient file or patient sheet.

A system for carrying out the method according to the invention comprises:

a. a measuring device for the non-invasive recording of measurement data of a body region to be examined in a measurement process;

b. at least one local terminal device with a display device; and c. a server for storing and forwarding received data; whereby the at least one local terminal device and the server are set up for the mutual exchange of data;

the at least one local terminal device is set up to receive measurement data from the measuring device and to generate and display image data from the received measurement data;

the at least one local terminal device is set up to transmit identification data and the image data to the server; and the at least one local terminal device is set up to retrieve stored image data from the server on the basis of identification data transmitted to the server and to display this retrieved image data during a measurement process.

When examining a patient, the same terminal device can always be used over time, or different devices can be used.

However, each of the devices is able to generate first measurement data and second measurement data as required. Preferably, the identification data is used to automatically recognize whether stored image data is already available and whether it should be retrieved and displayed. For example, the identification data is always transmitted to the server, which then returns either the stored image data and/or information about the existence of previous measurements or image data.

A preferred embodiment of the system according to the invention further comprises at least one reading device for reading an individual marking on the body region to be examined and for generating corresponding marking data, wherein the at least one local terminal device is set up to receive the marking data from the reading device and to generate the identification data from this marking data.

Again, the same reading device can always be used over time, or different devices can be used.

A computer program suitable for controlling a local terminal device of the system according to the invention comprises instructions which, when the program is executed by a computer, cause the computer to perform the following steps:

a. receiving first measurement data from a measuring device and generating and displaying first image data from the received first measurement data on a display device;

b. transmission of identification data and the first image data to a server;

c. transmission of second identification data to the server;

d. receive stored image data from the server using the transmitted second identification data;

e. display the received image data on the display device;

f. receiving second measurement data from the measuring device and generating and displaying second image data from the received second measurement data on the display device.

In a preferred variant, the computer program further comprises instructions to execute the following steps:

receiving first marking data from a reading device and generating the first identification data from the first marking data;

receiving second marking data from the reading device and generating the second identification data from the second marking data.

Further advantageous embodiments and combinations of features of the invention result from the following detailed description and the entirety of the patent claims.

BRIEF DESCRIPTION OF THE DRAWINGS

The drawings used to illustrate the embodiment example show.

In principle, identical parts are marked with identical reference signs in the figures.

DETAILED DESCRIPTION OF THE INVENTION

Figure 1:
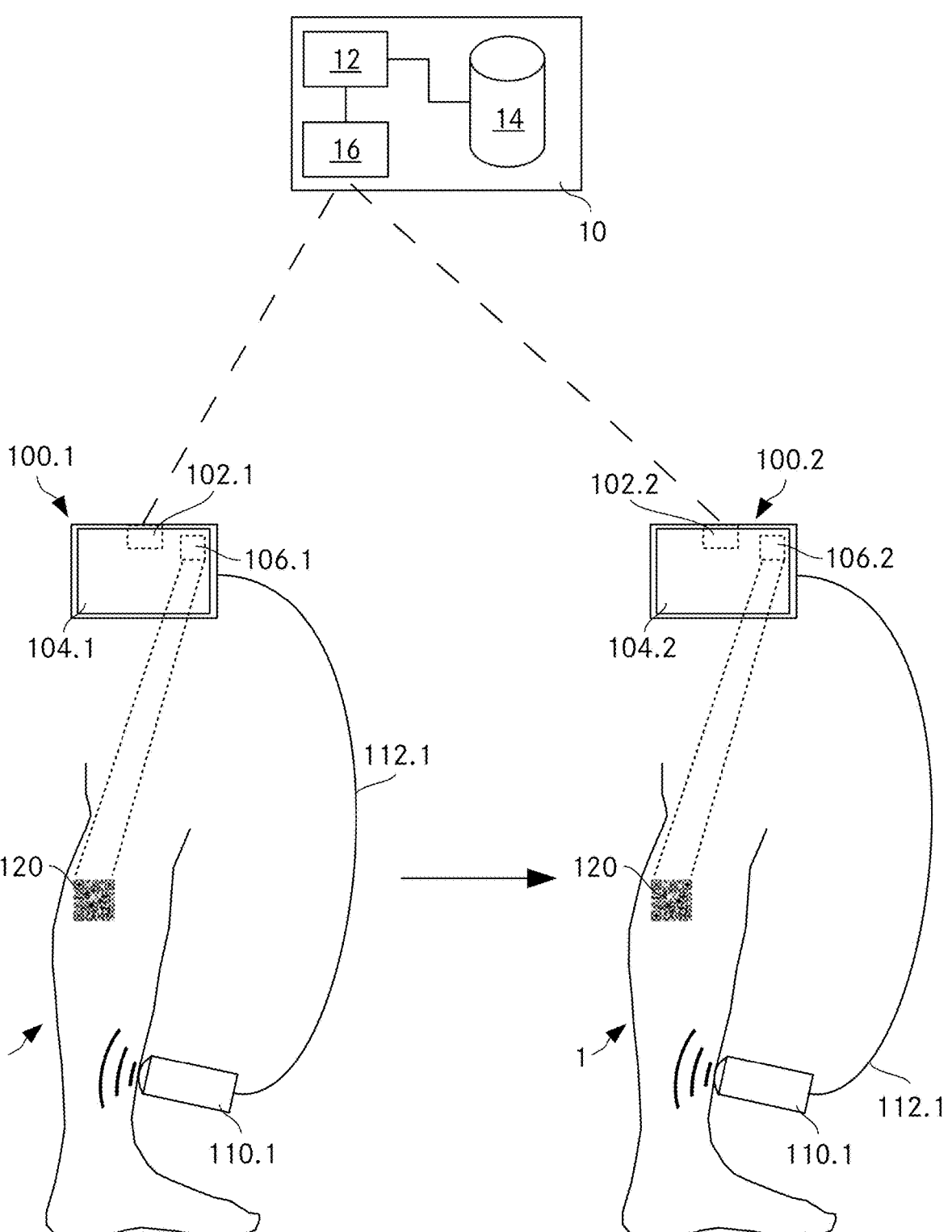
FIG. 1A schematic diagram illustrating one embodiment of the system according to the invention.

FIG. 1 is a schematic diagram illustrating one embodiment of the system according to the invention. The system comprises a server 10, which is a common computer system suitable for server operation. Among other things, it comprises a central processing unit 12, as well as a database 14 and a communication interface 16, which are connected to the central processing unit 12. The computer system is connected to a data network, in particular the Internet, and is protected against unauthorized access locally and from the outside using measures that are known as such. The database 14 or the storage of the corresponding data can be realized locally at the server 10 or in a cloud.

The server 10 communicates with several local terminal devices 100.1, 100.2. These are designed in particular as tablets and include a communication interface 102.1, 102.2, a touch screen 104.1, 104.2 and a camera 106.1, 106.2. Communication with the server 10 takes place via the communication interface 102.1, 102.2 via a secure Internet connection (secured e.g. with TLS). In particular, validated certificates are used to ensure that the data arriving at the server 10 originates from a local terminal device 100.1, 100.2.

The connection between the local terminal devices 100.1, 100.2 and the server 10 can be established directly, or a gateway server is located near the local terminal device 100.1, 100.2, with which the local terminal device communicates. This in turn then communicates with the server 10. The local terminal device 100.1, 100.2 is connected to the data network or the gateway server wirelessly, in particular via WLAN, a mobile phone connection or Bluetooth.

The system also includes measuring heads 110.1, 110.2, which are connected to a local terminal device 100.1, 100.2 via a cable 112.1, 112.2. The measuring head 110.1, 110.2 is supplied with electrical energy via the cable 112.1, 112.2, which is also used to exchange data with the local terminal device 100.1, 100.2. Alternatively, embodiments are also possible in which the measuring head comprises a local energy storage device, in particular a rechargeable battery, and data communication with the local terminal device is wireless, for example via a Bluetooth connection.

In the embodiment example shown, each of the measuring heads 110.1, 110.2 comprises an ultrasound measuring unit and a pressure measuring unit, as described, for example, in EP 3 716 842 A1 (Veinpress GmbH), i.e. ultrasound data can be generated for imaging and the contact pressure between the measuring head 110.1, 110.2 on the body surface can be determined and output simultaneously while the ultrasound data is being recorded. In the present case, the ultrasonic frequency is approx. 10 MHz, resulting in a resolution of approx. 0.07 mm. The required penetration depth is 5-10 cm. The contact pressure is determined via a force measurement, e.g. using a (MEMS) strain gauge, a capacitive measuring cell or a piezo measuring cell. The measuring range is 0-100 mmHg, for example. A measuring accuracy of 2-5% is required from a minimum pressure of 5 mmHg.

The corresponding measurement data are transmitted from the measuring head 110.1, 110.2 to the respective local terminal device 100.1, 100.2 in real time and synchronized with each other. Ideally, the transmission (and display) of the measurement data takes place at a frequency of 20 frames/s or more, so that a continuous display results for the operators.

As explained below, the following functionalities in particular are provided on the local terminal device 100.1, 100.2, controlled by corresponding software:

guiding the user through a corresponding user interface (GUI);

capture and process user input;

taking photos and determining identification data based on the photos taken;

power supply of the measuring head;

control of the measuring head 110.1, 110.2;

reception and processing of the ultrasonic data received by the 110.1, 110.2 measuring head;

reception and processing of the pressure data received from the 110.1, 110.2 measuring head;

presentation of processing results, including ultrasound images and pressure data; and bidirectional communication with the server 10.

Self-adhesive tags 120 are used in the system according to the invention. They comprise a dot-matrix code, e.g. a QR code, and can be stuck to the skin surface in this area to mark a body region. The adhesive used is selected so that the tags 120 remain on the skin surface for several hours to days. At the same time, skin irritation is avoided as far as possible and the tags 120 can be removed essentially painlessly as soon as they are no longer needed. Several tags 120 with the same code are provided for each body region. As mentioned, one of the tags 120 is stuck to the body region, while another can be stuck into a patient file, for example.

The present embodiment is explained using an application in which the anterior compartment in the left lower leg 1 of a patient is to be examined with regard to a possible compartment syndrome (loge syndrome).

Figure 2:
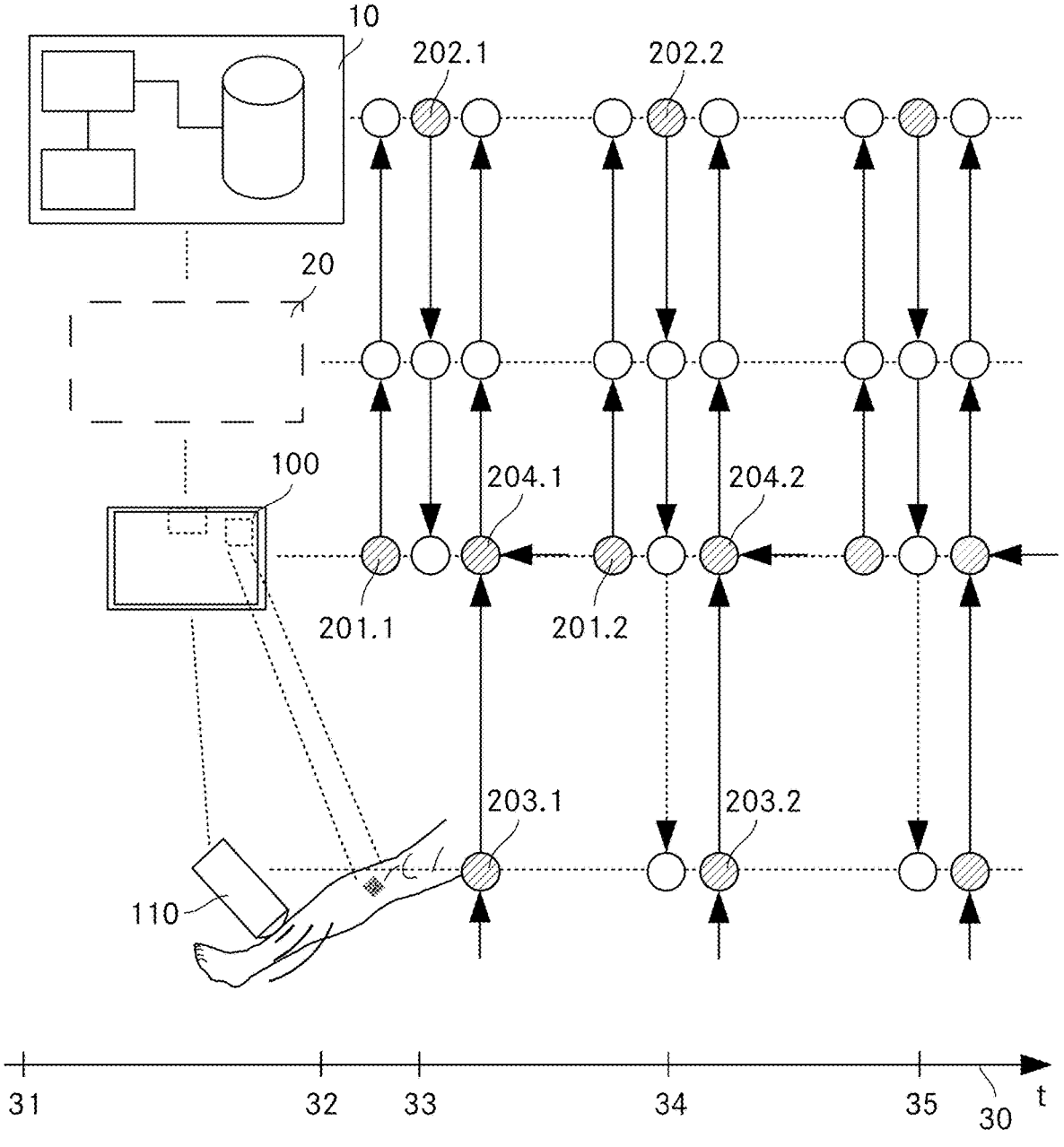
FIG. 2 a schematic representation of the data exchange during the execution of the method according to the invention.
Figure 3:
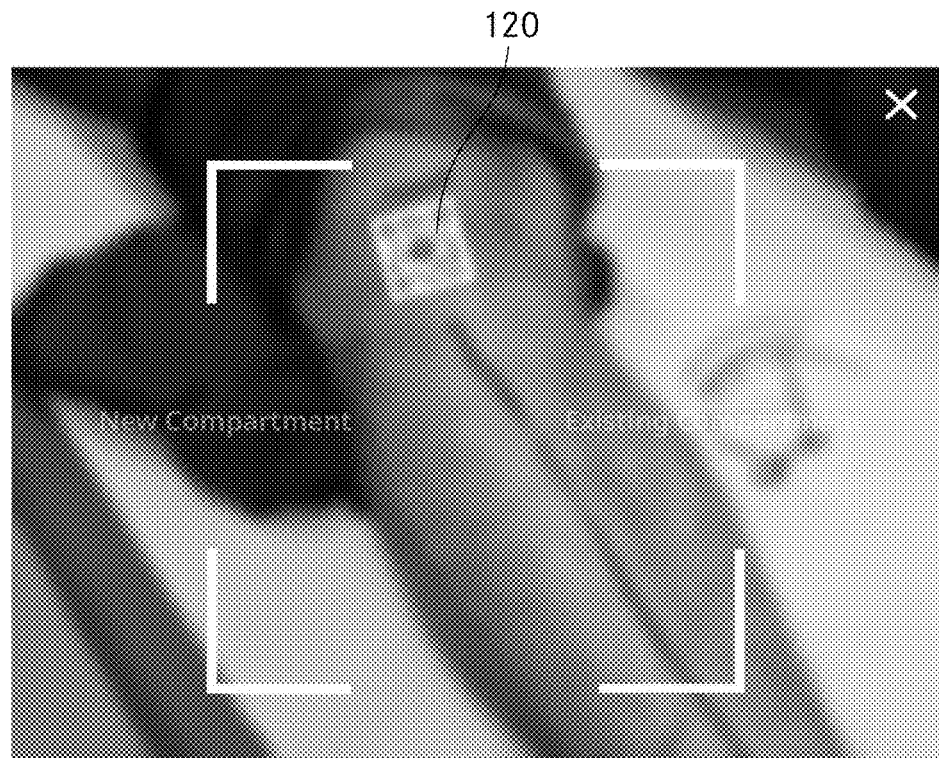
FIG. 3-18 representations of the user interface of the terminal device of the system according to the invention, when carrying out the method according to the invention.

FIG. 2 is a schematic representation of the data exchange during the execution of the method according to the invention. The most important data inputs and transmissions between the measuring head 110, the local terminal device 100, a local gateway 20 and the server 10 are shown along a time axis 30, starting with a traumatic impact (time 31). The local gateway 20 is used here only to forward data received from the server 10 to the local terminal device 100 (which may be one of several local terminal devices) or, conversely, to forward data received from the local terminal device 100 to the server 10. The gateway function is therefore not mentioned further below. As already noted, the system can also be implemented without a gateway 20; in this case, communication takes place directly between the local terminal device 100 and the server 10.

In general, the captured data is initially stored temporarily on the local terminal device 100. As soon as a connection to the server 10 is established, it is stored on the server (or the corresponding cloud service). The data is automatically deleted on the local terminal device 100, usually 2 weeks after the last access. In exceptional cases, if the local memory is no longer sufficient, the data is deleted before this period expires, starting with the oldest data. If necessary, the data is retrieved from the server.

The data also remains stored in the database or cloud for a specified-longer-period of time, unless it is deleted manually at the request of an authorized person.

The data stored in the database or in the cloud includes the following information in particular for each measurement performed:

time;

ID of the measurement;

ID of the tag (patient/body region);

position of the local terminal device used (via GPS or IP address);

image data of two images with different print values;

calibration and measurement parameters;

result values (e.g. CP score, see below).

FIGS. 3-18 are illustrations of the user interface of the terminal device of the system according to the invention, during the implementation of the method according to the invention. It should be noted that not all steps are illustrated, but only the most important ones.

The user interface is displayed on the touch screen 104.1, 104.2 of the local terminal device 100.1, 100.2. This is also used for user inputs, which can be made in a manner known per se by the interaction of one or more fingers of the user and/or a pen with the surface of the touch screen 104.1, 104.2. Further input means, e.g. buttons, may be provided. The touch screen may be set up to capture pressure-dependent inputs and/or provide haptic feedback. User guidance is supported by colors, but the user interface is shown in grayscale in FIGS. 3-17.

First, a tag 120 is applied to the body region to be examined, in this case to the lower leg, below the knee (time 32). The camera of the local terminal device 100 is now used to capture the stick-on tag (FIG. 3), and the local terminal device 100 decodes the corresponding dot-matrix code to obtain a unique identification character string (ID string). The local terminal device 100 transmits this ID string (data 201.1, 201.2) to the server 10 to check whether data linked to this ID string is already available. If this is the case, the data 202.2 is transferred from the server to the local terminal device. Otherwise, a response is sent (data 202.1) that no data is yet available and a new local data record is created on the local terminal device to which the ID string is assigned. In the following, it is assumed that no data was yet available on the server 10, i.e. an initial measurement is performed.

Figure 4:
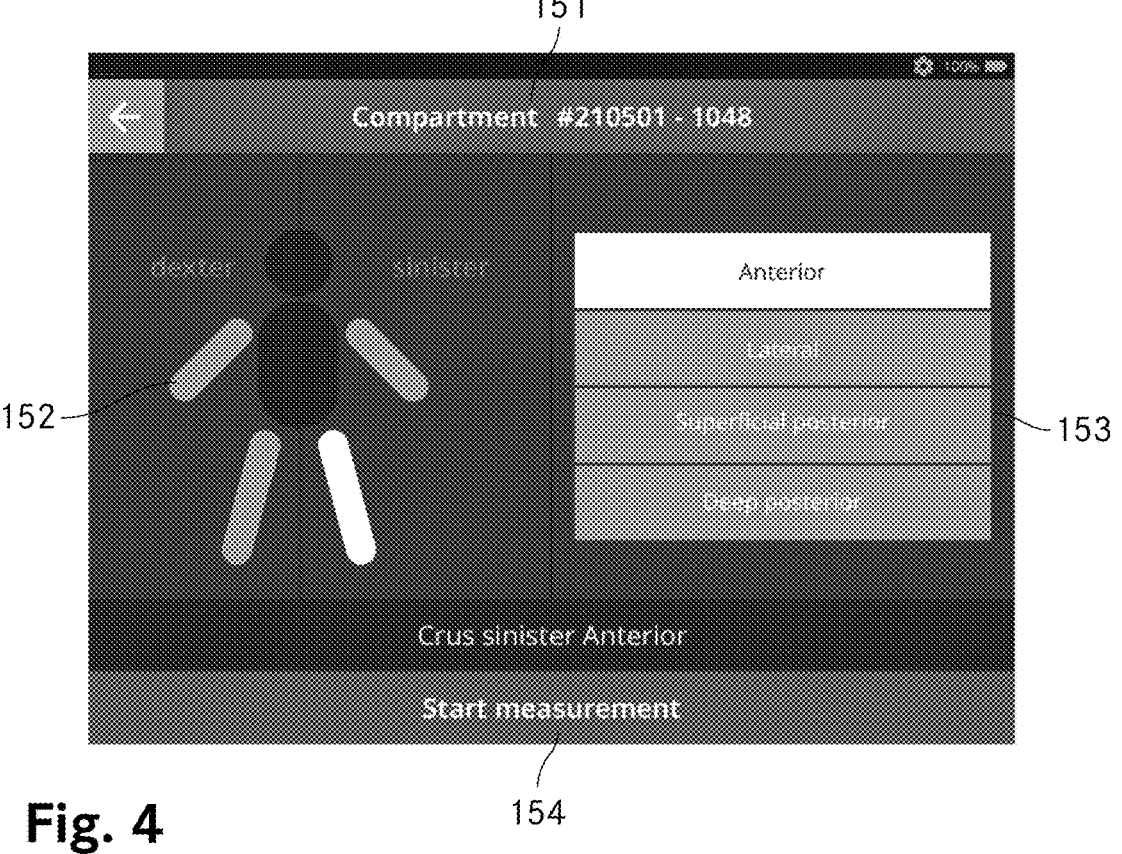

In the next display, as shown in FIG. 4, the ID string 151 is now displayed. The operator is asked to enter information about the body region to be examined. In this case, the operator selects the examined extremity from a schematic body diagram 152 (in this case the left leg). The compartments of this limb that can be examined are then displayed in a selection list 153 and the operator selects the corresponding compartment (in this case the anterior compartment in the lower leg). By pressing a now available button 154, the operator can start the measurement (time 33).

Figure 5:
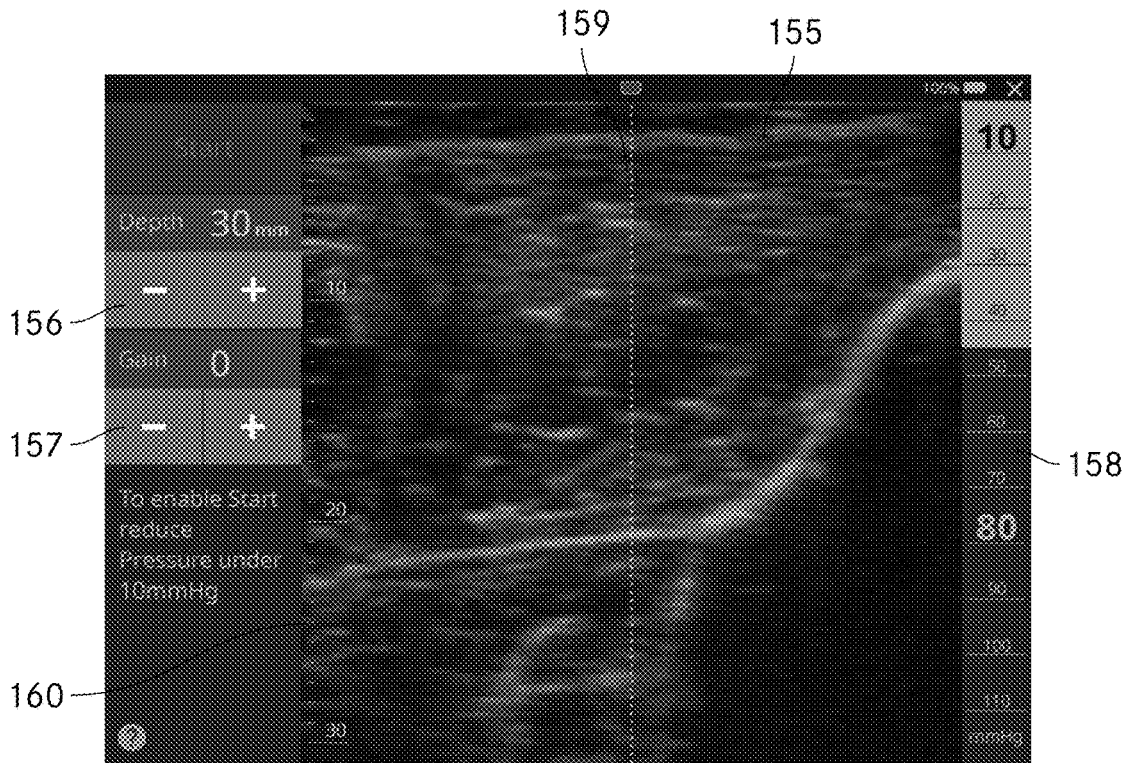

This is carried out with the aid of the measuring head 110, whereby the image data and print data generated by the measuring head 110 are transmitted to the local terminal device 100 in real time (data 203.1, 203.2). The local terminal device 100 now checks whether a measuring head 110 is correctly coupled to it. If this is not the case, a request is issued to connect a measuring head or to check it. As soon as the measuring head 110 is present, the operator is prompted to place it on the body part to be examined. As soon as ultrasound data that can be used for imaging is captured, the ultrasound image 155 is displayed in the user interface (FIG. 5). The ultrasound image 155 is the usual two-dimensional B-scan. In the corresponding display, the operator also has the option of setting the penetration depth and thus also the depth of the displayed image (Depth) using a controller 156 and the overall amplification (Gain) using a further controller 157. The operator is now also requested to reduce the contact pressure below 10 mmHg in order to start the actual measurement process. The contact pressure is shown on a scale 158, which runs from top to bottom on the right-hand edge of the image. The ultrasound image 155 also shows a central line 159 along the main detection direction of the ultrasound measuring head and a depth scale 160 on the left edge of the image.

Figure 6:
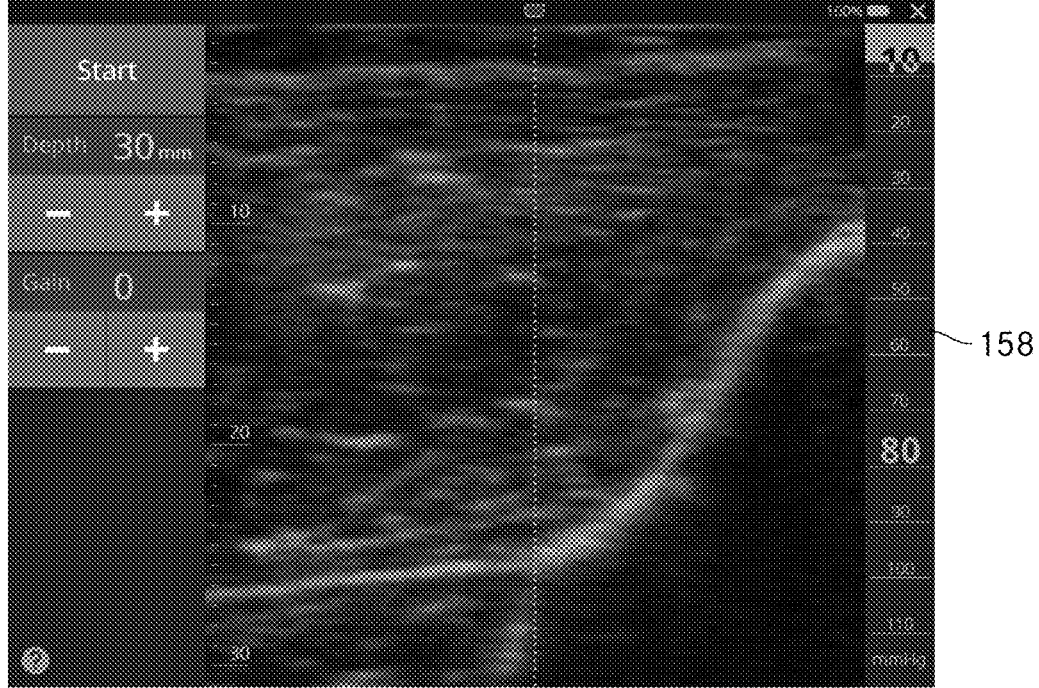
Figure 7:
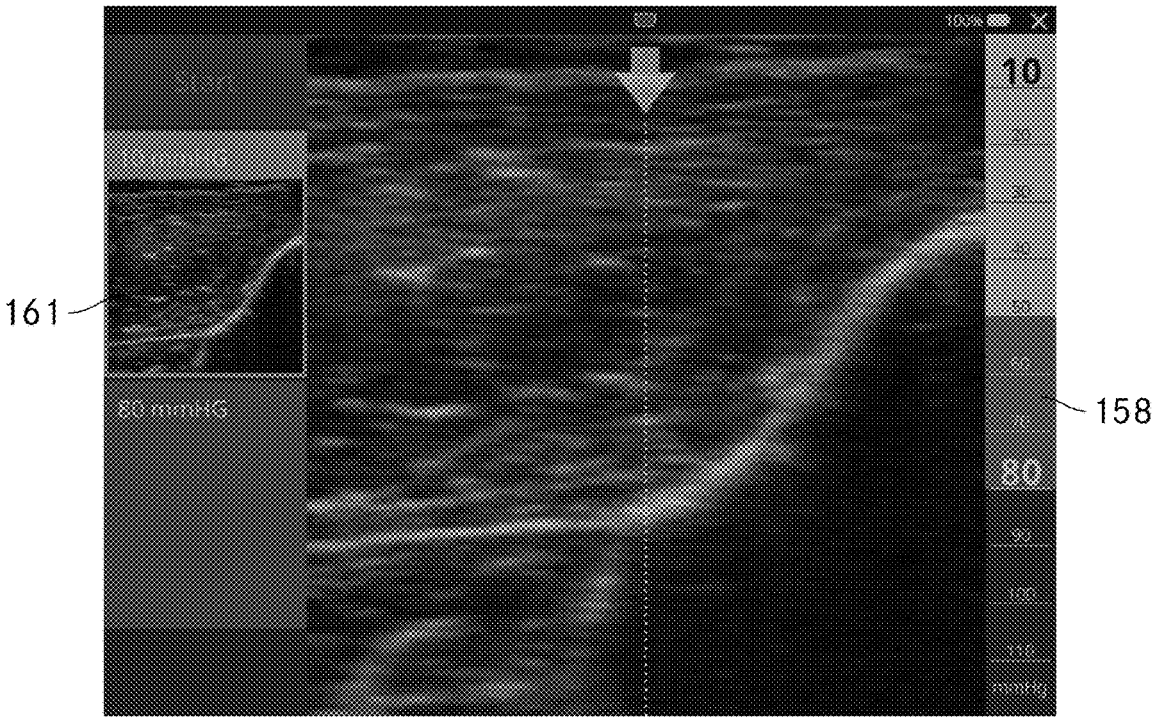
Figure 8:
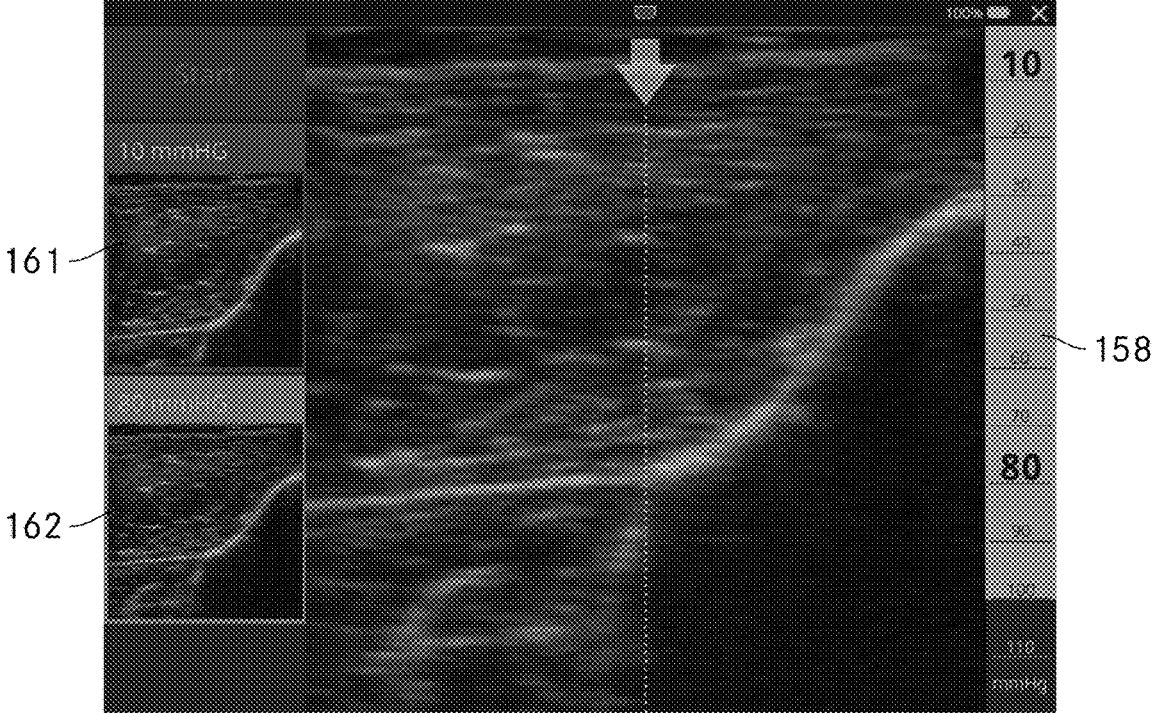

The operator thus locates the area to be examined and then reduces the contact pressure. As soon as the contact pressure has been reduced below 10 mmHg, as shown in FIG. 6, the measurement begins. The operator now successively increases the contact pressure, whereby the increase should take place within a time frame of approx. 1-3 seconds. As soon as the pressure corresponds to 10 mmHg, a first image is automatically saved and displayed in a corresponding image window 161 on the left side of the user interface (FIG. 7). The operator increases the contact pressure further. As soon as the pressure corresponds to 80 mmHg, a second image is automatically saved and displayed in another image window 162 below the first image window 161 (FIG. 8). The measuring process is now complete, which is confirmed to the operator in the user interface.

The values of the lower contact pressure and the upper contact pressure can be changed manually via the local terminal device if required. It is also possible to specify different combinations of values in the system for different compartments in order to capture the elastic properties in the best possible way.

Figure 9:
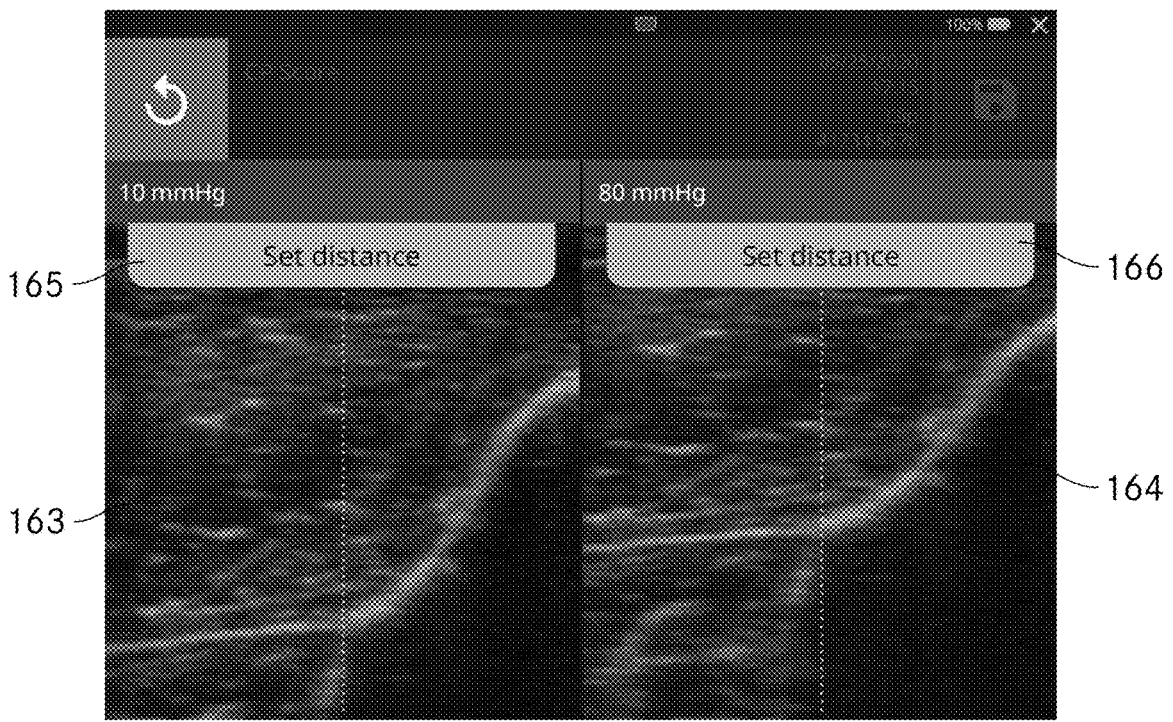

Next, the two images are displayed side by side in the user interface: A left image window 163 shows the image at a contact pressure of 10 mmHg, a right image window 164 shows the image at a contact pressure of 80 mmHg. The user can now select one of the image windows 163, 164 to mark a distance by pressing a corresponding button 165, 166 ("Set distance") (FIG. 9).

Figure 10:
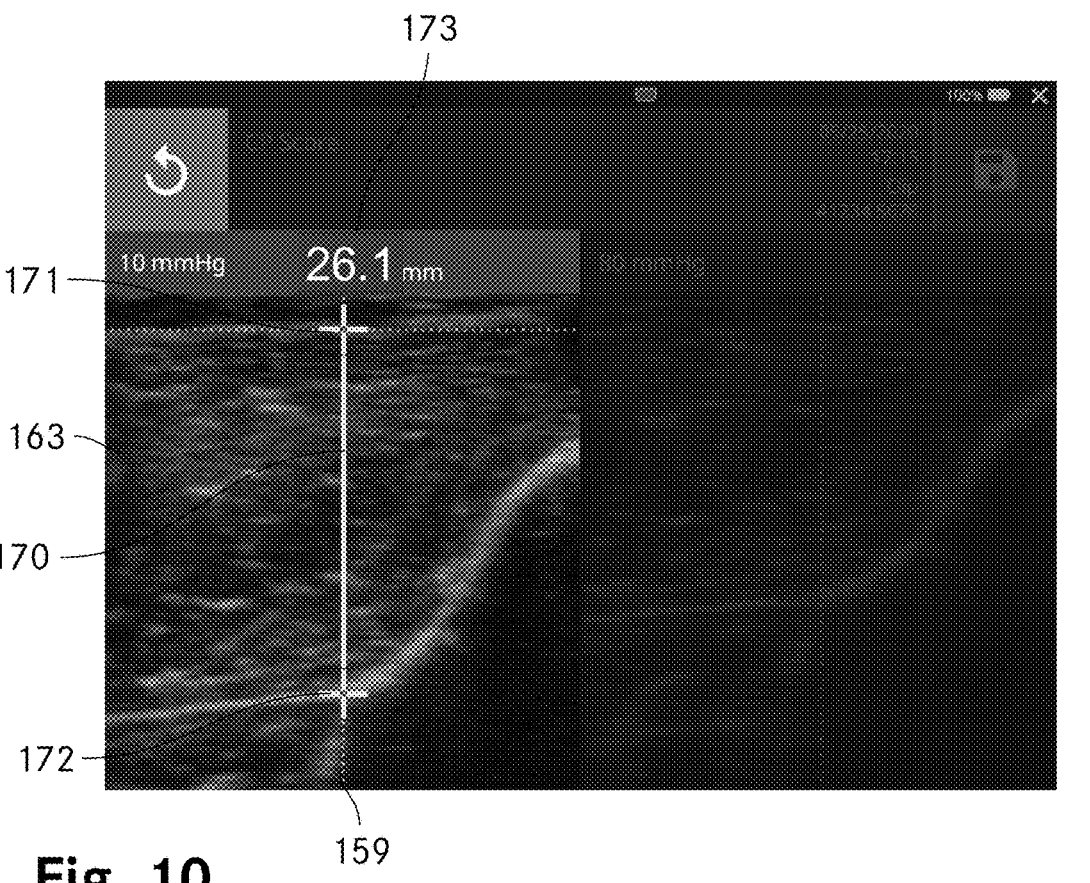
Figure 11:
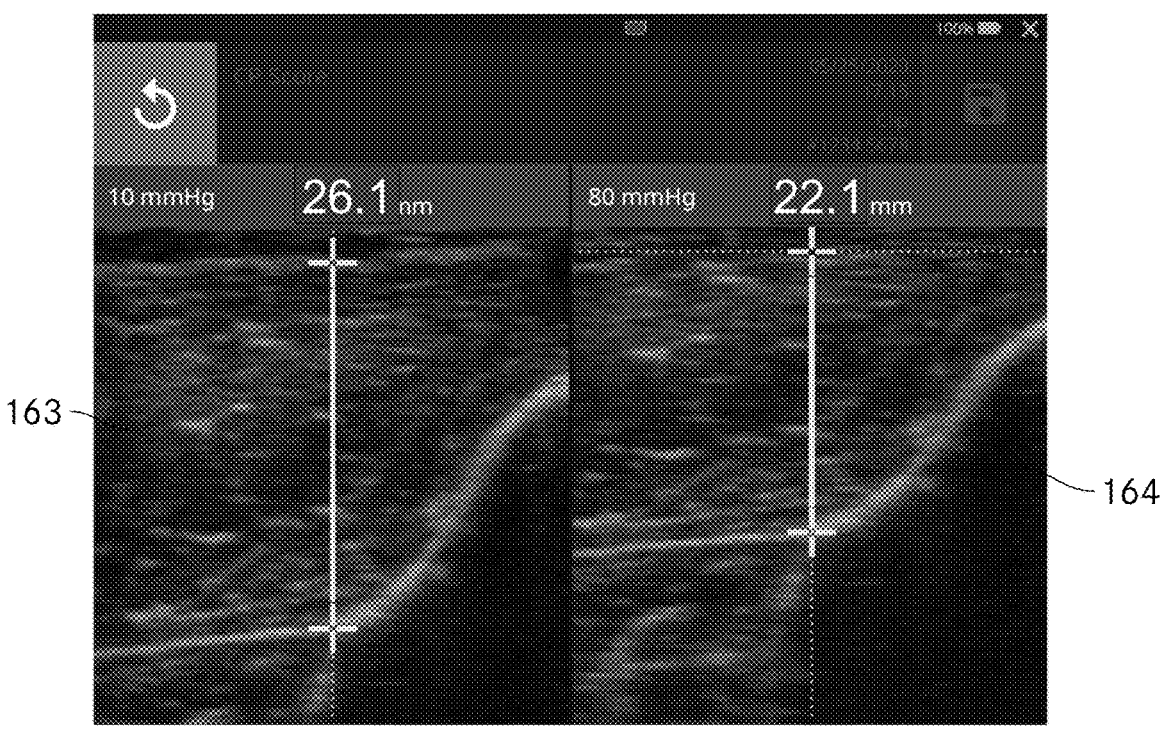

FIG. 10 shows how the distance is marked in the left image window 163: A line 170 along the central line 159 is provided with two crosshairs 171, 172. These can be moved upwards (towards the body surface) or downwards (away from the body surface) along the central line 159 using the touchscreen until their location corresponds to the boundary of the compartment to be examined. The distance between the two crosshairs 171, 172 is shown in a display area 173, here 26.1 mm. The same procedure is repeated for the second image in the right-hand image window 164. There, the distance is merely 22.1 mm for the situation with a contact pressure of 80 mmHg (see FIG. 11).

The crosshairs are positioned with pixel accuracy, which means an accuracy of approx. 0.1 mm, generally corresponding to the resolution of the ultrasound image. The positioning can be supported by additional displays and/or control elements, in particular by a line curve that represents the suitably averaged image brightness along the central line 159 and or buttons with which the crosshair position can be shifted up or down by one pixel at a time.

Depending on the requirements, the available resolution and the image area to be displayed, a zoom function can also be useful, with which the area in the area of a crosshair can be enlarged.

Figure 12:
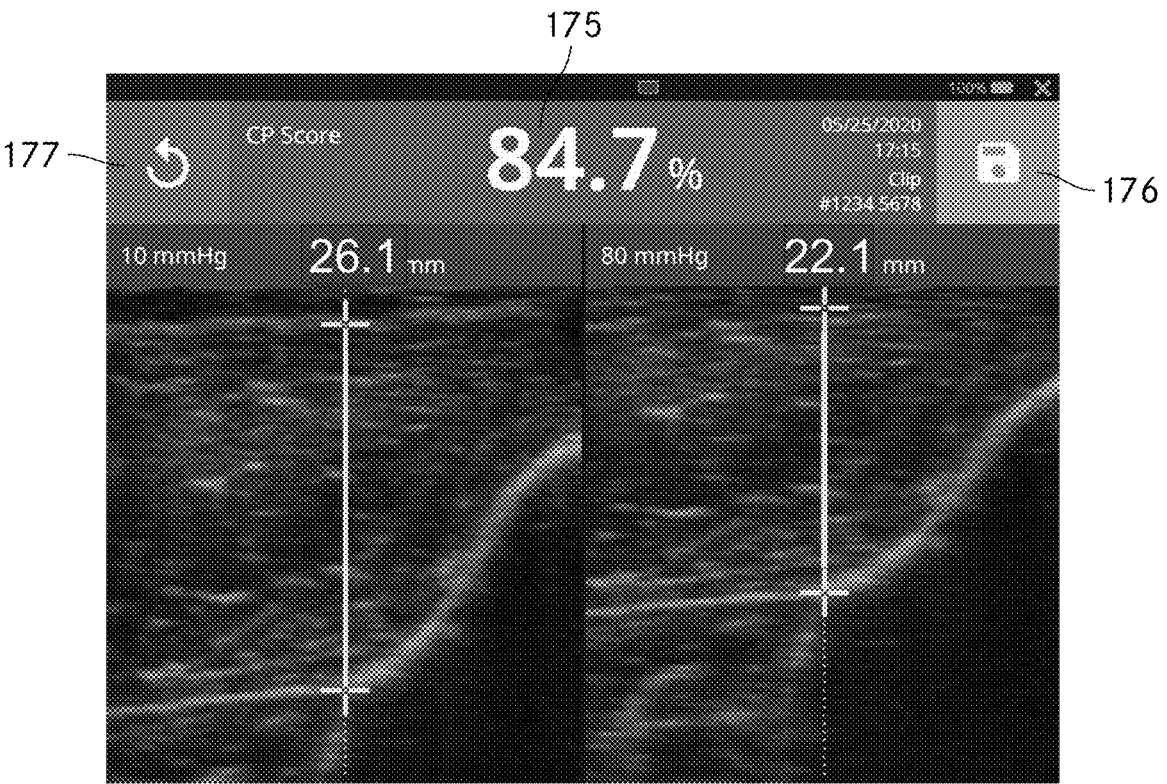

Based on the distances, the so-called "CP score" is now calculated as follows:

$$CP = 100 - 100 \cdot \frac{D_1 - D_2}{D_1} [\%],$$

where $D_1$ is the extent of the compartment along the central line 159 at the lower pressure of mmHg and $D_2$ is the extent of the compartment along the same line at the higher pressure of 80 mmHg. This value 175 is now displayed in the user interface (FIG. 12). The operator can now choose whether to complete the process and save the data (button 176) or whether to repeat the process (button 177).

Figure 13:
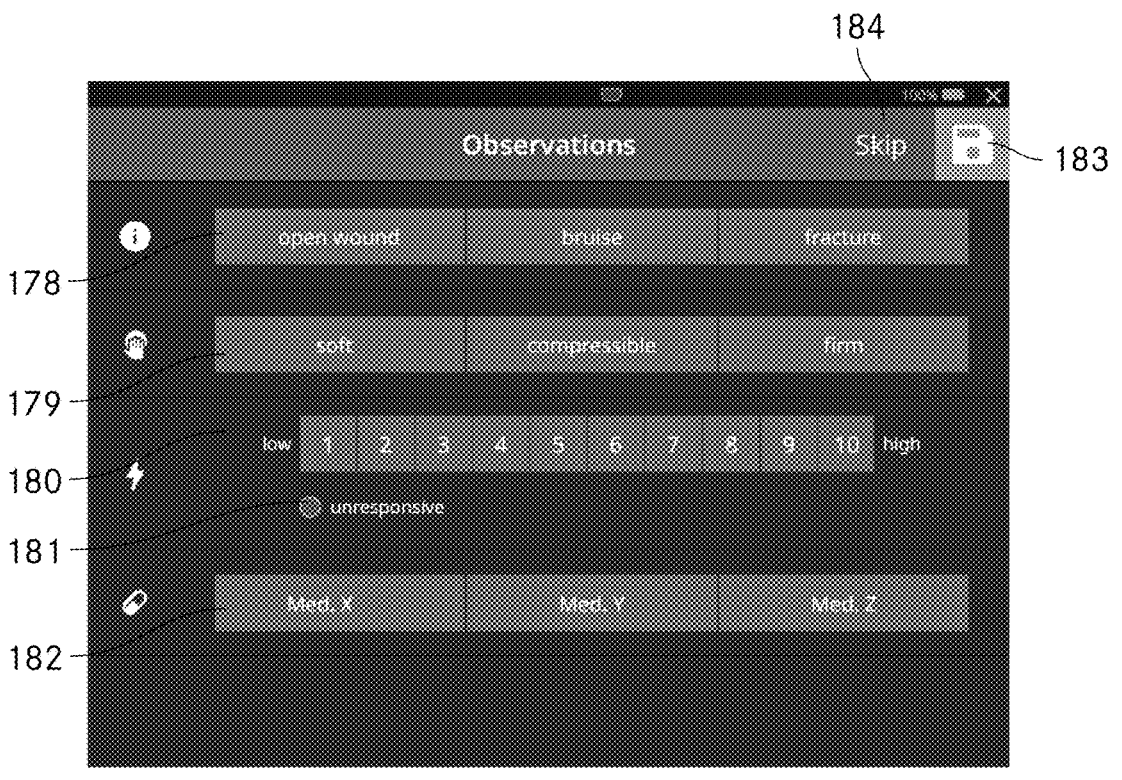

If the process is to be completed, the operator is given the opportunity to capture further information about the medical history for storage on the server. For this purpose, the user interface as shown in FIG. 13 is displayed, in which the following can be captured in a simple and systematic manner:

first selection element 178: type of traumatic injury (open wound, contusion, fracture);

second selection element 179: result of palpation (soft, elastic, firm);

third selection element 180: general state of health (scale from 1-10);

button 181: indication that the patient is unresponsive;

fourth selection element 182: information on medication.

The operator has the option of saving the captured data (button 183) or skipping this step altogether ("Skip") (button 184).

Figure 14:

The measurement is now shown in an overview diagram according to FIG. 14. The value 175 for the CP score is represented by a data point in a line diagram 185, supplemented by a date and time indication 186. Further information on the medical history can also be found in this display. Based on this display, the operator has the option of linking a new day to the measurement (or series of measurements) (button 187), exporting the data (button 188) or taking another measurement (button 189).

Figure 15:
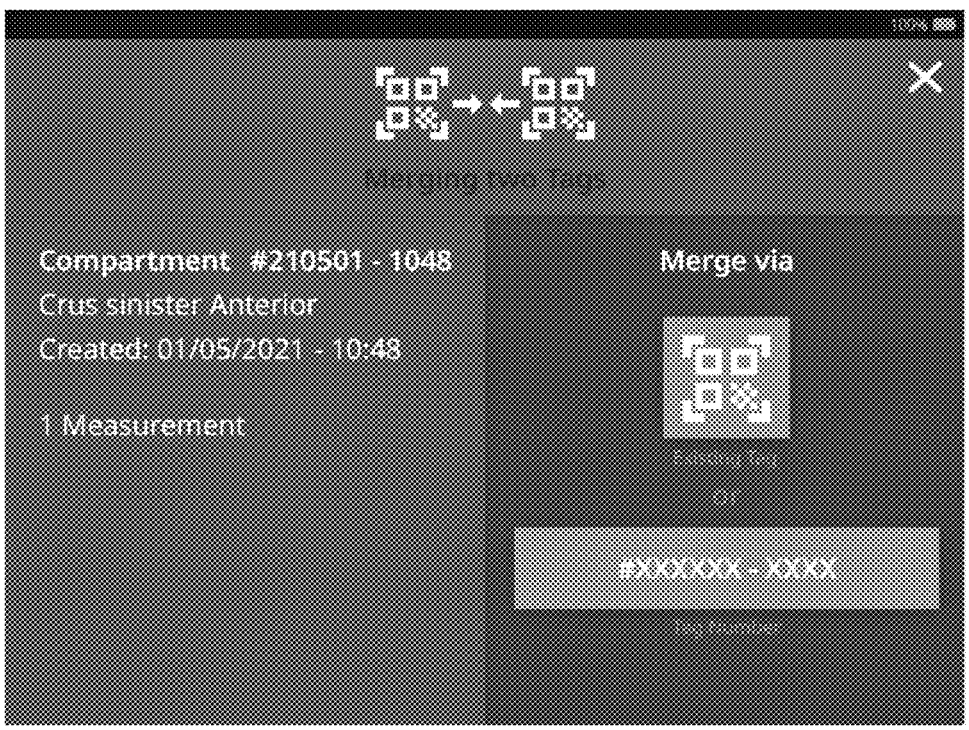
Figure 16:
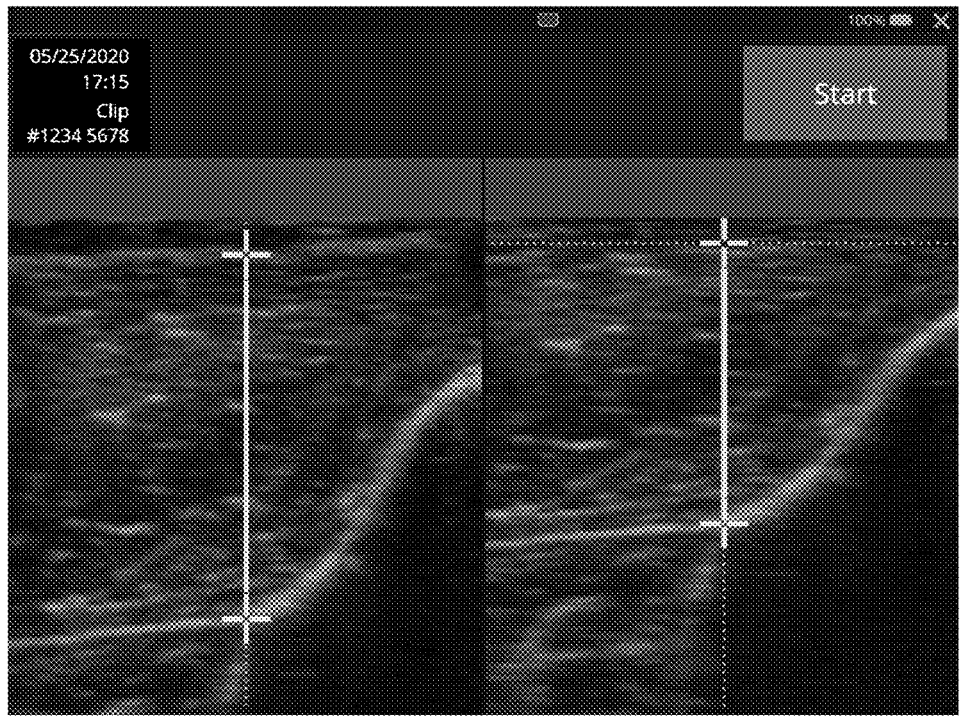

The user interface for linking a new tag is shown in FIG. 15. The previous tag can be captured by scanning this tag (e.g. in the patient file) or by entering the corresponding tag number.

The complete data 204.1, 204.2 of the measurement as listed above are transmitted to the server 10 after they have been completed.

Further measurements at the same location, at later points in time 34, 35, are carried out in the same way as the first measurement, using the same or a different terminal device. After scanning the tag, the information is retrieved from the server. Exceptionally, if the same terminal device is used as for the previous measurement at this body site and if no connection to the server can be established, the information stored locally on the terminal device is used. Capture of the ultrasound images at the specified pressure values is supported by displaying one of the images of a previous measurement process on the touchscreen of the local terminal device as a reference, including the central line and measurement distance (crosshairs), see FIG. 16 with the display of an image of the previous measurement process on the left and the display of the current view on the right. The operator can thus easily and precisely match the position of the current measurement with the position of a previous measurement.

Figures 17, 18:
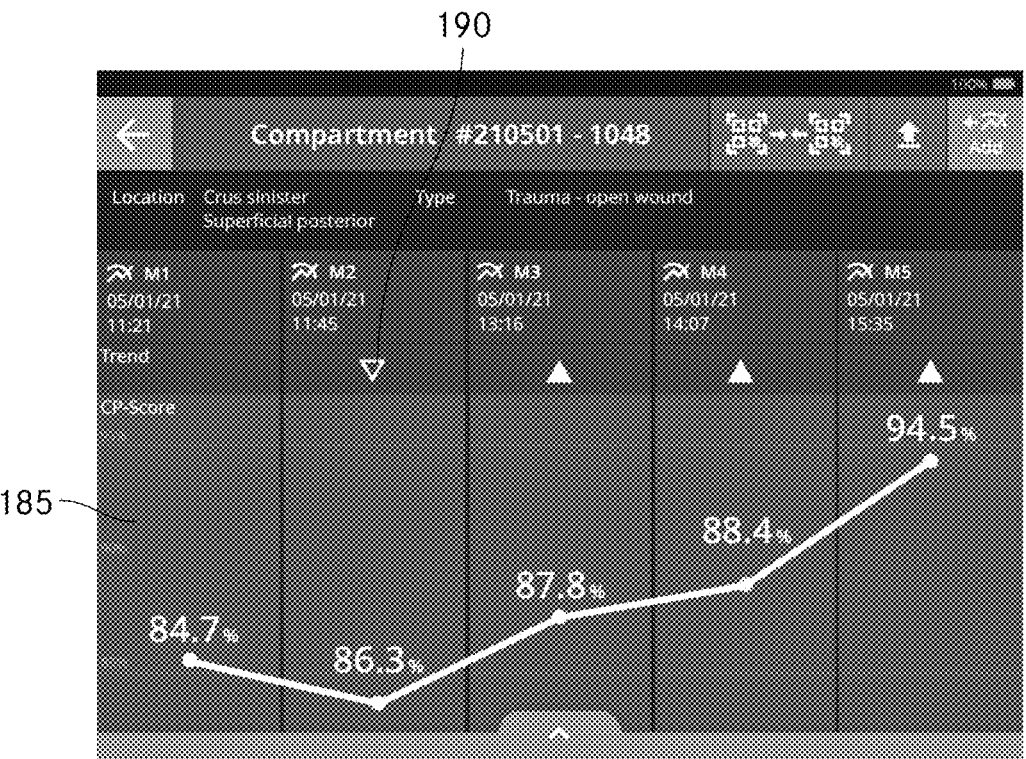

After several measurements have been taken, the overview display appears as shown in FIG. 17: Several data points in the line diagram 185 represent the CP scores of several measurements M1-M5. They are connected by a line, and the measurements (with the exception of the first one) are supplemented by a trend indication 190, which results from a comparison of the respective measurement with the previous measurement. A possible deterioration in the condition of the compartment, corresponding to an increase in the CP score, is highlighted by a filled arrow. The progression of the CP score can thus be intuitively captured at a glance.

The same local terminal device can be used to examine several compartments and/or patients in a staggered and/or consecutive manner, so that the terminal device and the server ultimately contain measurements from different people. These can be displayed on the terminal device in a list as shown in FIG. 18, where the CP score of the most recent measurement is displayed with a trend indication. The operator receives more detailed information on the corresponding compartment by selecting the corresponding line.

The local terminal device and the corresponding software are not absolutely necessary to access the information stored in the database 14 of the server 10. This is also possible—with the appropriate authorizations—via a secure web interface or an application programming interface (API). The API can be used to automatically transfer data to an electronic patient record. It may also be possible to supplement the information stored in the database 14 via an API.

The web interface enables various operations in connection with the stored data, in particular:

display the data in various display formats;

export the data in various export formats;

repeat the distance measurements to determine the CP score;

manual deletion of stored data;

manage users and devices;

billing functions;

generate and output usage statistics;

manage and install software and firmware updates;

consulting tutorials;

receiving user support.

Some of these functionalities can only be used via a special administrator interface or with appropriate access authorizations.

Access to the server, regardless of whether it takes place on a local terminal device, via a web or a programming interface, can be recorded in an electronic logbook. The corresponding entries can contain, for example, the user, the terminal device, the time and/or the data record viewed. In particular, the logbook can be stored on the server. The logbook can be used, for example, to generate statistics or carry out case-specific clarifications.

The invention is not limited to the embodiment shown. For example, additional data can be captured and processed, e.g. data on the time of a traumatic impact or other information on the medical history or photo or video data for documenting the examination process.

The distribution of capture, processing and output functions to the various system components can be selected differently. For example, the tag can be captured with a reading device or camera located in the measuring head instead of with the camera of the local terminal device.

Specific properties and operating parameters of the measuring head components can be selected differently depending on the application, e.g. the resolution and penetration depth of the ultrasonic system and the pressure range to be captured by the pressure measuring device.

As described above, a number of procedural steps can be automated or supported with the help of automated processes. In this context, the article by A. Crimi et al. "Automatic Measurement of Venous Pressure Using B-Mode Ultrasound", IEE Transactions on Biomedical Engineering, Vol. X, No. X, July 2015 describes methods for detecting tissue structures (specifically veins) and determining their internal pressure by collapsing them using variable external application forces. In particular, image processing and image recognition methods mentioned in this publication can also be used in the context of the present invention.

Also as described above, the repeated identification of the patient can be carried out in another way, e.g. using another machine-readable or non-machine-readable data carrier which is located in the area of the body region to be examined or outside this body region on the patient or is provided independently of this.

In summary, the invention provides a method for the non-invasive capture of the temporal development of a tissue structure, which provides improved basic information for diagnostic purposes based on several examinations at different times.

| List of reference symbols (not submitted) | |
| --- | --- |
| 1 | Lower leg |
| 10 | Server |
| 12 | Central processing unit |
| 14 | Database |
| 16 | Communication interface |
| 20 | Gateway |
| 30 | Timeline |
| 31 | Time |
| 32 | Time |
| 33 | Time |
| 34 | Time |
| 35 | Time |
| 102.1, 102.2 | Communication interface |
| 104.1, 104.2 | Touch screen |
| 106.1, 106.2 | Camera |
| 112.1, 112.2 | Cables |
| 100, 100.1, 100.2 | Terminal device |
| 110, 110.1, 110.2 | Measuring head |
| 120 | Day |
| 151 | ID string |
| 152 | Body diagram |
| 153 | Selection list |
| 154 | Button |
| 155 | Ultrasound image |
| 156 | Controller |
| 157 | Controller |
| 158 | Scale |
| 159 | central line |
| 160 | Depth scale |
| 161 | Image window |
| 162 | Image window |
| 163 | Image window |
| 164 | Image window |
| 165 | Button |
| 166 | Button |
| 170 | Line |
| 171 | Crosshairs |
| 172 | Crosshairs |
| 173 | Display area |
| 175 | Value |
| 176 | Button |
| 177 | Button |
| 178 | Election element |
| 179 | Election element |
| 180 | Election element |
| 181 | Button |
| 182 | Election element |
| 183 | Button |
| 184 | Button |
| 185 | Line diagram |
| 186 | Date and time |
| 187 | Button |
| 188 | Button |
| 189 | Button |
| 190 | Trend indication |
| 201.1, 201.2 | Data |
| 202.1, 202.2 | Data |
| 203.1, 203.2 | Data |
| 204.1, 204.2 | Data |

We claim:

1. A method for non-invasive capture of a temporal development of a state of a tissue structure comprising:

non-invasive recording of a first measurement data of a body region to be examined and generation of a first image data from the recorded measurement data, wherein the first measurement data include ultrasound data;

local pre-processing of the first image data using a first local terminal device;

transmitting the pre-processed first image data and a first identification data from the first local terminal device to a server for storage;

retrieving stored image data from the server using a second local terminal device based on a second identification data;

displaying the retrieved stored image data on the second local terminal device;

non-invasive recording of a second measurement data of the body region to generate a second image data, wherein a second examination to obtain the second measurement data is of the same kind as a first examination to obtain the first measurement data and wherein when the second measurement data is recorded, the second image data is displayed in real time on the second local terminal device, together with the retrieved stored image data, wherein the second measurement data include ultrasound data;

wherein the non-invasive recording of the first measurement data comprises a measurement of a contact pressure, wherein, in order to obtain information on an elastic state of the tissue structure, a determination of dimensions is carried out both in the first image data and in the second image data at at least two different contact pressure forces in each case, wherein a manual marking process is carried out on the displayed first image data and second image data to determine the dimensions.

2. The method according to claim 1, wherein the non-invasive recording of the first measurement data comprises a sonographic measurement process.

3. The method according to claim 1, wherein the preprocessed first image data are displayed on the local terminal device and further first measurement data are recorded based on the display.

4. The method according to claim 1, wherein a representation of an intensity curve of the first or second image data along a line is displayed to support the manual marking process.

5. The method according to claim 1, wherein a proposal for markings to be made during the manual marking process is automatically generated on the basis of the first or second image data.

6. The method according to claim 1, wherein the dimensions are determined automatically on the basis of the first image data or second image data.

7. The method according to claim 1, wherein a first value for the elastic state of the tissue structure is determined from the determined dimensions at the different contact forces based on the first measurement data and a second value for the elastic state of the tissue structure is determined from the determined dimensions at the different contact forces based on the second measurement data, the first value and the second value representing a measure for a deformability of the tissue structure.

8. The method according to claim 1, wherein time information is transmitted to the server for storage together with the pre-processed first image data and the first identification data.

9. The method according to claim 1, wherein a medically relevant point in time is captured and transmitted to the server for storage.

10. The method according to claim 9, wherein a recommendation is generated for a time of capturing the second measurement data, wherein the captured medically relevant point in time is taken into account for generating the recommendation.

11. The method according to claim 9, wherein the medically relevant point in time is a point in time of a traumatic impact.

12. The method according to claim 1, wherein before the first measurement data are recorded, the body region to be examined is provided with an individual marking, in that the marking is read by means of a first reading device and the first identification data are generated on the basis of the read marking, and in that before the stored image data are retrieved, the marking is read again by means of a second reading device and the second identification data are generated on the basis of the read marking.

13. The method according to claim 12, wherein a tag with a unique identification is attached to the body region to be examined in order to provide it with the individual marking.

14. The method according to claim 13, wherein the tag is stuck to the body region to be examined.

15. The method according to claim 12, wherein the first reading device and the second reading device are optical reading devices.

16. The method according to claim 15, wherein the optical reading devices are cameras.

17. Use of the method according to claim 1 for obtaining information on the elastic state of compartments.

18. The method according to claim 1, wherein the retrieved image data includes a marking created in the manual marking process on the first image data.

19. The method according to claim 1, wherein a location of the determination of dimensions is specified by an operator during the first measurement and is determined automatically during subsequent measurements.

20. The method according to claim 1, wherein a still image of a current ultrasound image is immediately generated when a predefined contact pressure value is reached.

21. The method according to claim 1, wherein a still image of a current ultrasound image is immediately generated when a predefined contact pressure value is reached and the still image is displayed for the subsequent manual marking process.

22. A system for non-invasive capture of a temporal development of a state of a tissue structure, comprising a measuring device for a non-invasive recording of measurement data of a body region to be examined in a measurement process, wherein the measurement data include ultrasound data;

at least one local terminal device with a display device; and a server for storing and forwarding received data; whereby the at least one local terminal device and the server are set up for the mutual exchange of data;

the at least one local terminal device is set up to receive the measurement data from the measuring device and to generate and display in real time image data from the received measurement data;

the at least one local terminal device is set up to transmit identification data and the image data to the server;

the at least one local terminal device is set up to retrieve stored image data from the server on the basis of the identification data transmitted to the server and to display this retrieved stored image data during a measurement process together with the image data generated from the received measurement data; and the at least one local terminal device is set up, in order to obtain information on an elastic state of the tissue structure, to carry out a determination of dimensions both in the image data generated from the received measurement data and in the retrieved stored image data at at least two different contact pressure forces in each case, wherein the at least one local terminal device is set up to enable a manual marking process being carried out on the displayed image data from the received measurement data and on the displayed retrieved stored image data to determine the dimensions.

23. The system according to claim 22, further comprising at least one reading device for reading an individual marking on the body region to be examined and for generating corresponding marking data, wherein the at least one local terminal device is set up to receive the marking data from the reading device and to generate the identification data from this marking data.

24. A computer configured to perform steps comprising:

receiving first measurement data from a measuring device, wherein the non-invasive recording of the first measurement data with the measuring device comprises a measurement of a contact pressure and generating and displaying first image data from the received first measurement data on a display device, wherein the first measurement data include ultrasound data;

transmission of identification data and the first image data to a server;

transmission of second identification data to the server;

receiving stored image data from the server using the transmitted second identification data;

displaying the received image data on the display device;

receiving second measurement data from the measuring device, wherein a second examination to obtain the second measurement data is of the same kind as a first examination to obtain the first measurement data, and generating and displaying second image data from the received second measurement data on the display device, and, when the second measurement data is recorded, displaying the second image data in real time on the display device, together with the retrieved stored image data, wherein the second measurement data include ultrasound data;

and, in order to obtain information on an elastic state of the tissue structure, determining dimensions both in the second image data and in the retrieved stored image data at at least two different contact pressure forces in each case, wherein to determine the dimensions, enabling to carry out a manual marking process on the displayed second image data and retrieved stored image data.

25. The computer according to claim 24, further configured to perform the following steps:

receiving first marking data from a reading device and generating the first identification data from the first marking data;

receiving second marking data from the reading device and generating the second identification data from the second marking data.

* * * * *